United States Patent [19]

Yunlu

[11] Patent Number: 5,783,676
[45] Date of Patent: Jul. 21, 1998

[54] SYNTHESIS OF SOLID, POWDERY RARE EARTH CARBOXYLATES BY A PRECIPITATION METHOD

[75] Inventor: Kenan Yunlu, Princeton, N.J.

[73] Assignee: Rhodia Inc., Cranbury, N.J.

[21] Appl. No.: 623,722

[22] Filed: Mar. 29, 1996

[51] Int. Cl.$^6$ ........................................... C07F 5/00
[52] U.S. Cl. ................................... 534/15; 534/16
[58] Field of Search ............................... 534/15, 16

[56] References Cited

U.S. PATENT DOCUMENTS

| | | | |
|---|---|---|---|
| 3,189,630 | 6/1965 | Smutny | 260/429.2 |
| 5,017,539 | 5/1991 | Jenkins et al. | 502/102 |
| 5,135,994 | 8/1992 | Anagnostou | 525/507 |
| 5,154,764 | 10/1992 | Cells et al. | 106/310 |
| 5,360,898 | 11/1994 | Jordaan et al. | 534/16 |
| 5,496,528 | 3/1996 | David et al. | 423/623 |
| 5,610,114 | 3/1997 | Robert et al. | |
| 5,612,427 | 3/1997 | Robert et al. | |

FOREIGN PATENT DOCUMENTS 599096  11/1993  European Pat. Off. ........ C08F 36/04

*Primary Examiner*—Gary E. Hollinden
*Assistant Examiner*—Dameron Jones
*Attorney, Agent, or Firm*—Katherine L. Carleton

[57] ABSTRACT

The invention relates to the production of solid, powdery carboxylates of Rare Earth elements, particularly Nd, La, Pr, and Ce, where the ligands coordinated to the metal are preferably long chain, branched carboxylic acids, most preferably 2-ethylhexanoic, neodecanoic (versatic) and naphthenic acids. The process involves batch precipitation of the product by utilizing Rare Earth water soluble salts, preferably Rare Earth nitrates, and salts of the carboxylic acid and washing the product with water, alcohol, water and alcohol mixtures or combinations thereof.

17 Claims, No Drawings

SYNTHESIS OF SOLID, POWDERY RARE EARTH CARBOXYLATES BY A PRECIPITATION METHOD

FIELD OF THE INVENTION

The invention relates to a method for producing solid, powdery Rare Earth carboxylates by precipitation.

BACKGROUND OF THE INVENTION

The production of solid, powdery carboxylates of Rare Earth elements with long chain (C6 to C32), branched carboxylic acids by precipitation yields an oily, sticky wax-like material which upon drying (60° to 90° C.) does not easily convert into a powdery material.

One reason for the sticky, oily consistency may be that during the formation part of the carboxylic acid starting material remains unreacted ("free acid"). The presence of the free acid can prevent the formation of powdery materials.

It would be beneficial to have a process which easily produces solid, powdery carboxylates of Rare Earth elements. Such a material would be easier to process, handle and ship. Additionally, it would provide greater flexibility for the formulator. Currently, Rare Earth carboxylates are produced and provided to the formulator in solvent, typically an organic solvent. This can cause formulation concerns when utilizing them in polymerizations. The product of the present invention is free of a fixed solvent, thus allowing selection of any solvent. The product is soluble in many different solvents. This allows greater definiteness for determining final composition parameters when utilized in polymerizations.

The object of the present invention is to provide such a process and product.

SUMMARY OF THE INVENTION

The invention relates to the production of solid, powdery carboxylates of Rare Earth elements, particularly Nd, La, Pr, and Ce, where the ligands coordinated to the metal are preferably long chain, branched carboxylic acids, most preferably 2-ethylhexanoic, neodecanoic (versatic) and naphthenic acids. The process involves batch precipitation of the product by utilizing Rare Earth water soluble salts, preferably Rare Earth nitrates, and salts of the carboxylic acid and washing the product with water, alcohol, water and alcohol mixtures or combinations thereof.

Unless otherwise stated, all parts or percents are by weight.

"Comprising" as used herein, means various components can be conjointly employed. Accordingly, the terms "consisting essentially of" and "consisting of" are embodied in the term comprising.

DETAILED DESCRIPTION OF THE INVENTION

The carboxylic acids suitable for use include aliphatic, cycloaliphatic and aromatic mono and polybasic carboxylic acids. The acids may be saturated or unsaturated, straight or branched chained. The organic carboxylic acids can be either natural or synthetic or mixtures thereof. Examples of natural acids, although usually refined, include straight and branched chain carboxylic acids and mixtures such as tall oil acids and cyclic carboxylic acids such as naphthenic acid. A variety of synthetic carboxylic acids and particularly aliphatic or alicyclic mono-carboxylic acids or mixtures thereof, are useful. Long chain, branched carboxylic acids are preferred.

The organic carboxylic acids preferably will contain from about 6 to about 32 carbon atoms, preferably from about 5 to about 18 and more preferably from about 8 to about 10, but when more than one of the acids is employed, carboxylic acids containing as little as about 5 carbon atoms or as little as 2 carbon atoms can be employed as one of the acids of the mixtures. Examples of useful organic carboxylic acids include isopentanoic acid, hexanoic acid, 2-ethyl butyric acid, nonanoic acid, decanoic acid, 2-ethyl hexanoic acid, iso octanoic acid, isononanoic acid, neodecanoic acid, lauric acid, palmitic acid, stearic acid, oleic acid, linoleic acid, and commercially available mixtures of two or more carboxylic acids such as naphthenic acids. The acid number for the preferred naphthenic acid is from about 160 to about 300 mg KOH/g.

Preferred carboxylic acids for use are neodecanoic acids (such as Versatic acid supplied by Shell and Neodecanoic Acid supplied by Exxon), 2-ethyl hexanoic acid, naphthenic acid, (preferably having an acid number of from about 160 to about 300 mg KOH/g), 2-methyl butanoic acid, 3-methyl butanoic acid, 2,2-dimethyl propanoic acid, 3,5 dimethyl hexanoic acid, 2-ethyl pentanoic acid, 2,5 dimethyl hexanoic acid, 3-ethyl hexanoic acid, 2,2,4-trimethyl hexanedioic acid, 3,3,4-trimethyl hexanedioic acid, 2,6-dimethyl octanoic acid, 4,6-dimethyl octanoic acid, 2,4,6-trimethyl octanoic acid, undecylenic acid, 2,4,6-trimethyl nonanoic acid, and 2,4,6-trimethyl nonacosonoic acid.

The most preferred carboxylic acids for use are naphthenic acid (preferably having an acid number of from about 160 to about 300 mg KOH/g), neodecanoic acid (also referred to as versatic acid), and 2-ethyl hexanoic acid.

The term "neodecanoic acid" as utilized herein refers to mixtures of branched carboxylic acids, generally predominately about 10 carbon atoms. These acid mixtures generally have an acid number of from about 310 to about 325 mg KOH/g. Commercially available neodecanoic acids are supplied by Shell under the tradename, "Versatic 10" and by Exxon under the name "Neodecanoic Acid".

These acids are well known and described in, for example Kirk-Othmer, Encyclopedia of Chemical Technology, fourth edition, John Wiley & Son, New York, 1993, Vol.5, pp.147–192, which is incorporated herein by reference.

The amount of carboxylic acid utilized may vary, although it is generally preferred that the molar equivalent ratio of Rare Earth element to carboxylic acid be at least about 1 to about 3.

A carboxylic acid salt solution is preferably prepared by reaction of the carboxylic acid with a base which is an alkali metal, alkaline earth metal or ammonium (preferably tetra (lower alkyl) ammonium) oxide, hydroxide, carbonate or hydrogen carbonate.

The base suitable for reaction with the carboxylic acid is preferably a hydroxide of an alkali metal of Group I, preferably lithium, sodium or potassium. Most preferably the base is a hydroxide of sodium.

Bases suitable for use include: sodium hydroxide, lithium hydroxide, potassium hydroxide, tetrabutyl ammonium hydroxide, tetra methyl ammonium hydroxide, and tetra ethyl ammonium hydroxide.

The reaction of carboxylic acid and base preferably occurs in the presence of water to form the carboxylic salt solution, i.e., water is the preferred reaction medium.

The carboxylic salt, preferably in the form of a salt solution, is then preferably reacted with a Rare Earth nitrate ($RE(NO_3)_3$) to produce the Rare Earth carboxylate solid which will precipitate out of solution. The Rare Earth nitrates suitable for use are the nitrates of group III B of the periodic table (lanthanide series). Suitable Rare Earth nitrates are, for example, the nitrates of lanthanum, cerium, praseodymium, neodymium, promethium, samarium, europium, gadolinium, terbium, dysprosium, holmium, erbium, thulium, ytterbium and lutetium. Preferred for use are the nitrates of neodymium, lanthanum, praseodymium and cerium (preferably Ce III). Other Rare Earth water soluble salts can be utilized such as Rare Earth chlorides.

It is most desirable to perform the process steps, production of the carboxylic salt and then reaction of the carboxylic salt with a Rare Earth nitrate, solely in water; however the use of other solvents can have a beneficial effect on the consistency of the material. Methanol or mixtures of water and methanol can be suitable solvent media. Although, one skilled in the art would recognize the unsuitability of the utilization of solely methanol or a mix of water and methanol when producing a Rare Earth versatate or neodeconoate since they are soluble in methanol. Thus, suitable solvent media includes water, methanol, water and methanol mixtures and combinations thereof. Preferably, the solvent medium is at least about 50% water. When water and alcohol mixtures are utilized a ratio of about 1 to about 1 is most preferred.

After reaction of the carboxylic salt with the Rare Earth nitrate, the product, the precipitated Rare Earth carboxylate is treated to remove by-products and solvent. This can be done by any conventional means although a washing treatment is preferred. Preferably, the product is washed with water, methanol, water and methanol mixtures or any combination thereof. When a water and methanol mixture is utilized, preferably the ratio of water to methanol is about 1 to about 1 or at least about 50% water. Then conventional filtering and drying steps are preferably undertaken. Drying can be carried out, for example, by use of a drying oven, screw drier or any suitable equipment for drying. The product when dried will generally comprise less than about 2% water, preferably less than about 1% water, and most preferably less than about 0.5% water.

The pH should be controlled in relation to the addition to form the carboxylic salt such that when the addition is complete the pH is from about 7.5 to about 12, preferably from about 11 to about 12.

Controlling the temperature of the reaction of the carboxylic salt with the Rare Earth nitrate is also important. The temperature of the reaction is generally less than about 25° C., preferably less than about 20° C., and most preferably less than about 10° C. General temperature ranges are from about −5° C. to about 25° C., preferably from 0° C. to about 25° C., more preferably from 0° C. to about 20° C. and most preferably from 0° C. to about 10° C.

The Rare Earth carboxylates produced by the process of the present invention when dried are characterized in that the particle size is less than about 1260 µm, preferably less than about 1250 µm and most preferably less than about 1200 µm. General particle size ranges are from about 100 to about 1260 µm and preferably from about 200 to about 1200 µm. The particle size can be measured by examining a representative sample, such as about 100 mg distributed/spread over a dry slide, utilizing an Olympus Optical Microscope Model No. PMG-3 with a Leco 2001 Image Analyzer, software version 2.02. The size range represents the size of the most representative smallest and largest particles/agglomerates in a sample. In the case of sticky or waxy materials the measurement by this method is not possible due to the large size of the agglomerates. The dried Rare Earth carboxylates preferably comprise less than about 5%, more preferably less than about 4%, and most preferably less than about 3%, free acid as determined by acid base titration. Further, the Rare Earth carboxylates can provide excellent properties as raw materials for making catalysts. Catalysts made from the products of the present invention have excellent and/or improved properties for utilization in polymerization of conjugated dienes, especially 1,3-butadiene, isoprene and 2-methyl-1,3 pentadiene. They have low water content and good stability. Fields of application include any appropriate for the utilization of poly butadiene, for example in the manufacture of tires and technical rubber articles.

A process for the production of solid, powdery Rare Earth carboxylates according to the present invention comprising the steps of:

a) reacting a carboxylic acid with a base to form a carboxylic salt; and b) reacting said carboxylic salt with a water soluble Rare Earth salt to form a Rare Earth carboxylate in the presence of a solvent which is selected from the group consisting of water, methanol, and mixtures thereof; wherein the reaction temperature of step b is from about −5° C. to about 25° C., the pH of the reaction of step a ranges from about 7.5 to about 12 and the particle size of the product after drying is less than about 1260 µm.

Products of this process are preferably utilized as raw materials for the production of catalysts suitable for the polymerization of conjugated dienes, such as butadiene or isoprene. A preferred method for polymerizing conjugated dienes comprises polymerizing the conjugated diene in the presence of a catalytic amount of a Zieglar-Natta catalyst which is prepared utilizing the product of the present invention. Any conventional polymerization method can be utilized with Zieglar-Natta catalysts prepared utilizing the products of the present invention with good effect.

The following examples are provided to better describe and define the process and product of the present invention. They are for illustrative purposes and it is realized that changes or variations may be made with respect to these compositions that are not shown below. Such changes which do not materially alter the compositions, formulation, process or function are still considered to fall within the spirit and scope of the invention as recited by the claims that follow.

EXAMPLE 1

Synthesis of solid neodymium 2-ethylhexanoate solvent: water/methanol react.temp.: 25° C.

pH: 11.6

Procedure:

In a 150 ml beaker add 50 g water, 1.24 g NaOH solution (50.2%) and 2.31 g 2-ethylhexanoic acid (MW 144.21) and stir for about 5 min. The clear solution (pH 11.6) is then charged with 50 g of methanol. 3.02 g $Nd(NO_3)_3$ solution (Nd content 25.02%) is mixed with 10 g of a 50% aqueous methanol solution and added in a period of about 5 minutes to the sodium salt. A white precipitate is formed immediately and the mixture is stirred for an additional 5 minutes. The precipitate is then filtered by using a Buchner funnel under house vacuum (about 10 torr). The time required for filtration is about 10 minutes. The cake is washed 3 times with 50 g of a 50% aqueous methanol solution, filtered and finally is washed with 10 g of methanol and filtered. The yield of the product before drying is 5.4 g. The product is dried for about 15 hours at about 70° C. to give 2.8 g (yield 93.4%) of a bluish powder consisting of particles in the size range of from about 100 to about 500 μm.

Analytical data as measured by conventional methodology:
Nd content: 24.64%
water: 0.82%
free acid: 0.35%
$NO_3^-$: neg.

EXAMPLE 2

Synthesis of solid neodymium 2-ethylhexanoate solvent: water/methanol
react.temp.: 0° C.
pH: 11.6

In a comparative experiment, the synthesis is carried out at about 0° C., while the other conditions remain the same as described in Example 1. The product is obtained in 96.4% yield and has a similar powdery consisting of particles ranging in size from about 100 to about 600 μm.

Analytical data as measured by conventional methodology:
Nd content: 24.4%
water: 0.57%
free acid: 0.7%
$NO_3^-$: neg.

EXAMPLE 3

Synthesis of solid neodymium 2-ethylhexanoate solvent: water
react.temp.: 25° C.
pH: 11.6
Procedure:

In a 2 L beaker, a solution of sodium 2-ethylhexanoate with a pH of 11.6 is prepared by addition of 22.3 g of 2-ethylhexanoic acid [MW 144.21] (diluted with 200 mL deionized water) to 12.5 g of NaOH (50/50 w/w%, diluted with 600 mL deionized water). A solution of $Nd(NO_3)_3$ (30.17 g, 25.025 Nd) and deionized water (100 mL) is added to the clear sodium 2-ethylhexanoate in a period of about 15 minutes. A white precipitate is formed immediately and is stirred for about an additional 10 minutes. The precipitate is filtered by Büchner funnel under house vacuum (about 10 torr). Filtration requires approximately 10 minutes. The solid is washed three times with deionized water, 200 mL aliquots, and a final wash with 100 mL methanol. The product is dried for 16 hours at about 90° C. to give 27.20 g, 90.7% yield, of a bluish powder consisting of particles in the range of from about 200 to about 900 μm.

Analytical data as measured by conventional methodology:
Nd content: 24.2%
water: 0.16%
free acid: 3.25%
$NO_3^-$: neg.

EXAMPLE 4

Synthesis of solid neodymium 2-ethylhexanoate solvent: water
react.temp.: 0° C.
pH: 11.6
Procedure:

In a comparative experiment, the synthesis is performed at about 0° C., while all other conditions remain the same as in Example 3. The product is obtained in 88% yield and has a similar powdery consistency with a particle size range of from about 200 to about 1000 μm.

Analytical data as measured by conventional methodology:
Nd content: 24.5%
water: 0.21%
free acid: 1.2%
$NO_3^-$: neg.

EXAMPLE 5

Synthesis of solid neodymium 2-ethylhexanoate solvent: water
react.temp.: 25° C.
pH: 6.4
Procedure:

In a 2 L beaker, a 6.5% molar excess (24.1 g) of 2-ethylhexanoic acid is added to 12.5 g of NaOH (50/50 w/w%, diluted with 600 mL deionized water) to make a room temperature solution of sodium 2-ethylhexanoate with a pH of 6.4. A solution of $Nd(NO_3)_3$ (30.17 g, 25.025 Nd) and deionized water (100 mL) is added to the clear sodium 2-ethylhexanoate in a period of about 10 minutes. A white precipitate is formed immediately and is stirred for an additional 10 minutes. The precipitate is filtered by Büchner funnel under house vacuum (about 10 torr). Filtration required approximately 10 minutes. The solid is washed three times with deionized water using 200 mL aliquots. The product is dried for about 16 hours at about 70° C. to give 28.58 g, 95.3% yield, of a bluish, sticky powder consisting of particles with a size of greater than 1300 μm.

Analytical data as measured by conventional methodology:
Nd content: 24.5%
water: 1.24%
free acid: 5.22%
$NO_3^-$: pos.

EXAMPLE 6

Synthesis of solid neodymium octoate
Comparative example utilizing the procedure from EP 0 599 096 A1 solvent: water
react.temp.: 90° C.
pH: 7.3
Procedure:

A solution of sodium octoate with a pH of 7.3 is prepared by addition of 8 g of NaOH (50.2%, diluted with 200 g distilled water), to 31.6 g 2-ethylhexanoic acid [MW 144.21]. The temperature of this solution is then brought to 90° C. 24 g of $NdCl_3 (H_2O)_6$ is dissolved in 100 ml distilled water and is charged with diluted HCl solution (about 15%) until the pH reaches 1.7. The $NdCl_3$ solution is added to the sodium octoate solution in a period of about 18 minutes, while keeping the temperature around 90° C. The product, which precipitates out immediately consists mainly of big lumps. The material is then filtered by using a Buchner funnel and washed three times with a total volume of 250 ml of hot water. The product is dried at about 90° C. for about 15 hrs to give 38.4 g (99.9%) of a wax-like product consisting of lumps with an average particle size of about 5 mm.

Analytical data as measured by conventional methodology:
Nd content: 24.74%
water: 0.13%
free acid: 1.9%

EXAMPLE 7

Synthesis of solid neodymium versatate solvent: water
react.temp.: 0° C.
pH: 11.6
Procedure:

In a 2 liter beaker, 12.1 g of NaOH (50.2%) solution is diluted with distilled water to give a volume of 940 ml. The solution is charged with 26.39 g of versatic acid (MW 173.1) to yield a clear solution with a pH of 11.58. The volume of the solution is then increased to 1600 ml by addition of ice water. The beaker is placed into a salt/ice water bath in order to maintain a temperature of about 0° C. The agitation is carried out by using a mechanical stirrer with a rpm of about 550. 29.18 g $Nd(NO_3)_3$ solution (Nd content 25.02%) is mixed with ice water to bring the volume to 200 ml. The cold Nd nitrate solution is added to the sodium versatate solution by using a dropping funnel. Time required for complete addition is about 35 min. The mixture is stirred for an additional 10 min and then filtered by using a Buchner funnel under house vacuum (about 10 torr). Time required for filtration is 1 to 2 min. The wet material is washed 3 times with 450 ml of cold (5° C.) water and dried for about 15 hrs at 70° C. and then for about 1 hr at about 90° C. to yield 28.4 g (85%) of a non-sticky powder consisting of particles ranging from about 200 to about 1200 µm.
Analytical data as measured by conventional methodology:
water: 0.18%
free acid: 0.23%
Nd: 21.68%
$NO_3^-$: neg.

EXAMPLE 8

Synthesis of solid neodymium versatate solvent: water
react.temp.: 8°–10° C.
pH: 11.6

In a comparative experiment, the synthesis is carried out at temperatures of from about 8° to about 10° C. while all other conditions are kept the same as described in Example 7, except the concentration of the reaction mixture is three times higher (using only ⅓rd of the total water quantity). The product is obtained in 90.5% yield as a fine powder consisting of particles in a size range of from about 200 to about 1000 µm.
Analytical data as measured by conventional methodology:
water: 0.7%
free acid: 0.13%
Nd: 22.9%
$NO_3^-$: pos.

EXAMPLE 9

Synthesis of solid neodymium versatate react.temp.: 70° C.
pH: 11.6
Procedure:

In a 1 liter beaker, 6.05 g of NaOH (50.2%) solution is diluted with distilled water to give a volume of about 800 ml. The solution is charged with 12.84 g of versatic acid (MW 173.1) to yield a clear solution with a pH of 11.59. After bringing the temperature of the solution up to 70° C. 14.59 g of the Nd nitrate solution [ Nd content 25.02%, diluted with water to give 100 ml] is added in a period of about 15 min. A milk like slurry is formed immediately and towards the end of the addition the product turns into lumps. After agitating for another 5 minutes, the material is filtered by using a Buchner funnel and is washed three times with a total amount of 400 ml distilled water. The wet material is dried at about 70° C. for about 12 hrs and then at about 90° C. for about 3 hrs to give 15 g (90%) of a slightly sticky product consisting of lumps having an average particle size of about 5 mm.
Analytical data as measured by conventional methodology:
water: 0.24%
free acid: 6.0%
Nd: 21.82%
$NO_3^-$: neg.

EXAMPLE 10

Synthesis of solid neodymium neodecanoate solvent: water
react.temp.: 1° C.
Procedure:

In a 2000 ml beaker add 12.1 g of a NaOH solution (50.2%) and 26.36 g neodecanoic acid (MW 173.5) and distilled water to give a volume of 600 ml. After stirring for 5 minutes the clear solution is cooled down to about 1° C. 29.2 g of Nd nitrate solution [Nd content 25%, diluted with water to give 100 ml; temperature 1° C.] is added to the sodium neodecanoate solution in a period of about 5 minutes. After agitating for an additional 5 minutes the precipitate is filtered by using a Buchner funnel and is washed 3 times with a total amount of 400 ml of ice water. The product is dried for about 15 hrs at about 90° C. to give 31.3 g (93.4%) of a bluish powder having an average particle size of about 1100 µm.
Analytical data as measured by conventional methodology:
water: 0.1%
free acid: 0.7%
Nd: 21.3%

EXAMPLE 11

Synthesis of solid neodymium naphthenate solvent: water
react.temp.: 15° C.
Procedure:

In a 2000 ml beaker add 12 g of a NaOH solution (50.2%) and 35.69 g naphthenic acid (MW 237/AN 256) and distilled water to give a volume of 300 ml. After agitating for about 15 minutes the slurry is charged with 300 g methanol and cooled down to about 15° C. by using ice water. 28.96 g of Nd nitrate solution [Nd content 25.02%, diluted with 50 g water and 50 g methanol] is added to the sodium naphthenate solution in a period of about 15 minutes. After agitating for an additional 10 minutes, the precipitate is filtered by using a Buchner funnel and is washed twice with a total amount of 200 ml of aqueous methanol (50/50%)

solution. The product is dried for about 15 hrs at about 55° C. to give 40.6 g (94.9%) of a pale blue powder having a particle size of from about 600 to about 1000 μm.

Analytical data as measured by conventional methodology:

water: 0.44% free acid: 2.8%

Nd: 17.33%

$NO_3^-$: neg.

What is claimed:

1. A process for the production of solid, powdery Rare Earth carboxylates comprising the steps of:
   a) reacting a carboxylic acid with a base to form a carboxylic salt; and
   b) reacting said carboxylic salt with a water soluble Rare Earth salt to form a Rare Earth carboxylate in the presence of a solvent which is selected from the group consisting of water, methanol, and mixtures thereof, wherein a reaction temperature of step b is from about −5° C. to about 25° C., a pH of the reaction of step a ranges from about 7.5 to about 12 and a particle size of said Rare Earth carboxylate is less than about 1260 μm.

2. A process according to claim 1 wherein:
   a) said carboxylic acid is selected from the group consisting of straight and branched chain carboxylic acids and mixtures thereof; and
   b) said water soluble Rare Earth salt is selected from the group consisting of Rare Earth nitrates and Rare Earth chlorides.

3. A process according to claim 2 wherein said Rare Earth salt is a Rare Earth nitrate selected from the group consisting of nitrates of lanthanum, yttrium, cerium, praseodymium, neodymium, promethium, samarium, europium, gadolinium, terbium, dysprosium, holmium, erbium, thulium, ytterbium and lutetium.

4. A process according to claim 3 wherein said Rare Earth nitrate is selected from the group consisting of nitrates of neodymium, lanthanum, praseodymium, and cerium III.

5. A process according to claim 2 wherein said carboxylic acid is selected from the group consisting of neodecanoic acid (versatic acid), 2-ethyl hexanoic acid, naphthenic acid, 3-5 dimethyl hexanoic acid, 2,5 dimethyl hexanoic acid, 3-ethyl hexanoic acid, 2,2,4-trimethyl hexanoic acid, 3,3,4-trimethyl hexanoic acid, 2,6-dimethyl octanoic acid, 4,6-dimethyl octanoic acid, 2,4,6-trimethyl octanoic acid, 2,3,6-trimethyl nonanoic acid, 2,4,6-trimethyl nonacosonoic acid, 2-ethyl pentanole acid, 2-methyl butyric acid and undecylenic acid.

6. A process according to claim 5 wherein said carboxylic acid is selected from the group consisting of naphthenic acid, neodecanoic acid (versatic acid), and 2-ethyl hexanoic acid.

7. A process according to claim 1 wherein said base is selected form the group consisting of alkali metal hydroxide, alkali metal carbonate, alkali metal hydrogen carbonate, alkaline earth metal hydroxide, alkaline earth metal carbonate, alkaline earth metal hydrogen carbonate, ammonium hydroxide, ammonium carbonate, and ammonium hydrogen carbonate.

8. A process according to claim 1 wherein the base is a hydroxide of an alkali metal of Group I of the periodic table.

9. A process according to claim 8 wherein the base is a hydroxide of lithium, sodium, ammonium or potassium.

10. A process according to claim 9 wherein the base is a hydroxide of sodium or potassium.

11. A process according to claim 9 wherein said reaction temperature of step b ranges from 0° C. to about 10° C.

12. A process for the production of solid, powdery Rare Earth neodecanoates and versatates comprising the steps of:
   a) reacting a carboxylic acid selected from the group consisting of neodecanoic acid and versatic acid with a base selected from the group consisting of a hydroxide of lithium, sodium or potassium in a solvent which is water to obtain a carboxylic salt;
   b) reacting said caboxylic salt with a Rare Earth nitrate selected from the group consisting of nitrates of neodymium, lanthanum, praseodymium and cerium in a solvent which is water at a temperature of from 0° C. to about 25° C. to obtain a Rare Earth carboxylate; and
   c) treating said Rare Earth carboxylate to remove reaction by products and solvents by washing with water and then drying; wherein a pH of reaction step a ranges from about 7.5 to about 12 and a particle size of said Rare Earth Carboxylate is less than about 1260 μm.

13. A process for the production of solid, powdery Rare Earth carboxylates comprising the step of: reacting a carboxylic salt with a Rare Earth salt at a reaction temperature of from about −5° C. to about 25° C. to form a Rare Earth carboxylate.

14. The process of claim 13 wherein said Rare Earth carboxylate has a particle size of less than about 1260 μm.

15. A process for the production of solid, powdery Rare Earth carboxylates comprising the step of: reacting a carboxylic salt, which has been prepared by reacting a carboxylic acid with a base, with a water soluble Rare Earth salt in the presence of a solvent which is selected from the group consisting of water, methanol and mixtures thereof at a reaction temperature of from about −5° C. to about 25° C. to form a Rare Earth carboxylate.

16. The process of claim 15 wherein the Rare Earth salt is selected from the group consisting of Rare Earth nitrates, Rare Earth chlorides and mixtures thereof; the solvent is water; and the Rare Earth carboxylate has a particle size of less than about 1260 μm.

17. The process of claim 1 wherein said Rare Earth carboxylate comprises less than about 5% free acid.

* * * * *

(12) REEXAMINATION CERTIFICATE (4543rd)
United States Patent
Yunlu

(10) Number: US 5,783,676 C1
(45) Certificate Issued: Mar. 12, 2002

(54) SYNTHESIS OF SOLID, POWDERY RARE EARTH CARBOXYLATES BY A PRECIPITATION METHOD

(75) Inventor: Kenan Yunlu, Princeton, NJ (US)

(73) Assignee: Rhodia Rare Earths Inc., Shelton, CT (US)

Reexamination Request:
No. 90/005,859, Nov. 16, 2000

Reexamination Certificate for:
Patent No.: 5,783,676
Issued: Jul. 21, 1998
Appl. No.: 08/623,722
Filed: Mar. 29, 1996

(51) Int. Cl.$^7$ .................................................. C07F 5/00
(52) U.S. Cl. ............................................ 534/15; 534/16
(58) Field of Search ...................... 534/10–16; 502/170; 554/72

(56) References Cited

U.S. PATENT DOCUMENTS 5,449,387 A  9/1995  Hawkins et al.

*Primary Examiner*—Michael Hartley

(57) ABSTRACT

The invention relates to the production of solid, powdery carboxylates of Rare Earth elements, particularly Nd. La. Pr. and Ce, where the ligands coordinated to the metal are preferably long chain, branched carboxylic acids, most preferably 2-ethylhexanoic, neodecanoic (versatic) and naphthenic acids. The process involves batch precipitation of the product by utilizing Rare Earth water soluble salts, preferably Rare Earth nitrates, and salts of the carboxylic acid and washing the product with water, alcohol, water and alcohol mixtures or combinations thereof.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 12, 13 and 15 are determined to be patentable as amended.

Claims 2–11, 14, 16 and 17, dependent on an amended claim, are determined to be patentable.

1. A process for the production of solid, powdery *trivalent* Rare Earth carboxylates comprising the steps of:
   a) reacting a carboxylic acid with a base to form a carboxylic salt; and
   b) reacting said carboxylic salt with a water soluble *trivalent* Rare Earth salt to form a *trivalent* Rare Earth carboxylate in the presence of a solvent which is selected from the group consisting of water, methanol, and mixtures thereof, wherein a reaction temperature of step b is from about −5° C. to about 25° C., a pH of the reaction of step a ranges from about 7.5 to about 12 and a particle size of said *trivalent* Rare Earth carboxylate is less than about 1260 µm.

12. A process for the production of solid, powdery *trivalent* Rare Earth neodecanoates and versatates comprising the steps of:
   a) reacting a carboxylic acid selected from the group consisting of neodecanoic acid and versatic acid with a base selected from the group consisting of a hydroxide of lithium, sodium or potassium in a solvent which is water to obtain a carboxylic salt;
   b) reacting said carboxylic salt with a *trivalent* Rare Earth nitrate selected from the group consisting of nitrates of neodymium, lanthanum, praseodymium and cerium in a solvent which is water at a temperature of from 0° C. to about 25° C. to obtain a *trivalent* Rare Earth carboxylate; and
   c) treating said *trivalent* Rare Earth carboxylate to remove reaction [by products] *byproducts* and solvents by washing with water and then drying; wherein a pH of reaction step a ranges from about 7.5 to about 12 and a particle size of said *trivalent* Rare Earth Carboxylate is less than about 1260 µm.

13. A process for the production of solid, powdery *trivalent* Rare Earth carboxylates comprising the step of: reacting a carboxylic salt with a *trivalent* Rare Earth salt at a reaction temperature of from about −5° C. to about 25° C. to form a *trivalent* Rare Earth carboxylate.

15. A process for the production of solid, powdery *trivalent* Rare Earth carboxylates comprising the step of: reacting a carboxylic salt, which has been prepared by reacting a carboxylic acid with a base, with a water soluble *trivalent* Rare Earth salt in the presence of a solvent which is selected from the group consisting of water, methanol and mixtures thereof at a reaction temperature of from about −5° C. to about 25° C. to form a *trivalent* Rare Earth carboxylate.

* * * * *